United States Patent
Walker et al.

(10) Patent No.: US 6,719,724 B1
(45) Date of Patent: Apr. 13, 2004

(54) CENTRAL VENOUS LINE CATHETER HAVING MULTIPLE HEAT EXCHANGE ELEMENTS AND MULTIPLE INFUSION LUMENS

(75) Inventors: Blair D. Walker, Mission Viejo, CA (US); Scott M. Evans, Santa Ana, CA (US); Wayne A. Noda, Mission Viejo, CA (US)

(73) Assignee: Alsius Corporation, Irvine, CA (US)

( * ) Notice: Subject to any disclaimer, the term of this patent is extended or adjusted under 35 U.S.C. 154(b) by 0 days.

(21) Appl. No.: 09/816,645

(22) Filed: Mar. 23, 2001

Related U.S. Application Data

(63) Continuation-in-part of application No. 09/253,109, filed on Feb. 19, 1999.

(51) Int. Cl.$^7$ .......................... A61F 7/12; A61M 31/00; A61M 37/00
(52) U.S. Cl. ............. 604/113; 604/101.01; 604/101.03; 604/101.5; 606/21; 607/96; 607/106
(58) Field of Search ................................ 604/507–509, 604/96.01, 97.01, 99.01, 101.01, 101.03, 101.05, 103.06, 103.07, 113, 114, 174–180, 523, 912, 915, 916, 921; 606/20–28, 31, 194; 607/21, 96, 98–99, 104–106; 128/898; 137/340, 334

(56) References Cited

U.S. PATENT DOCUMENTS

| | | | |
|---|---|---|---|
| 4,164,943 A | * | 8/1979 | Hill et al. .................... 604/174 |
| 4,941,475 A | * | 7/1990 | Williams et al. ............. 600/505 |
| 5,122,113 A | | 6/1992 | Hattler |
| 5,182,317 A | | 1/1993 | Winters et al. |
| 5,207,640 A | | 5/1993 | Hattler |
| 5,242,390 A | | 9/1993 | Goldrath |
| 5,262,451 A | | 11/1993 | Winters et al. |
| 5,271,743 A | | 12/1993 | Hattler |
| 5,279,598 A | | 1/1994 | Sheaff |
| 5,383,856 A | | 1/1995 | Bersin |
| 5,423,763 A | | 6/1995 | Helland et al. |
| 5,478,309 A | | 12/1995 | Sweezer et al. |
| 5,501,663 A | | 3/1996 | Hattler et al. |
| 5,549,552 A | | 8/1996 | Peters et al. |
| 5,549,559 A | | 8/1996 | Eshel |
| 5,674,287 A | * | 10/1997 | Slepian et al. .............. 128/898 |
| 5,797,869 A | | 8/1998 | Martin et al. |
| 5,800,375 A | | 9/1998 | Sweezer et al. |
| 5,807,342 A | | 9/1998 | Musgrave et al. |
| 5,879,316 A | | 3/1999 | Safar et al. |
| 5,902,274 A | | 5/1999 | Yamamoto et al. |
| 5,906,588 A | | 5/1999 | Safar et al. |
| 6,190,356 B1 | | 2/2001 | Bersin |
| 6,231,594 B1 | | 5/2001 | Dae |
| 6,287,326 B1 | | 9/2001 | Pecor |

* cited by examiner

*Primary Examiner*—Brian L. Casler
*Assistant Examiner*—Catherine S. Williams
(74) *Attorney, Agent, or Firm*—John L. Rogitz

(57) ABSTRACT

An intravenous catheter system (apparatus and method) for controlling patient temperature includes a generally tubular elongated body having lumens for circulating a heat exchange fluid in a plurality of heat exchange elements provided at spaced intervals along the length of the elongated body. The heat exchange elements preferably comprise inflatable balloons. Heat exchange occurs between the fluid in the balloons and blood in the blood vessel. Each balloon preferably is sized such that, when inflated, each balloon blocks no more than approximately 30% to 75% of the blood vessel in which it is intubated. The catheter preferably has two to four balloons, each of which may have a different shape. The catheter also preferably has three to five infusion lumens for providing access to the patient's blood at different locations in the patient's bloodstream.

93 Claims, 15 Drawing Sheets

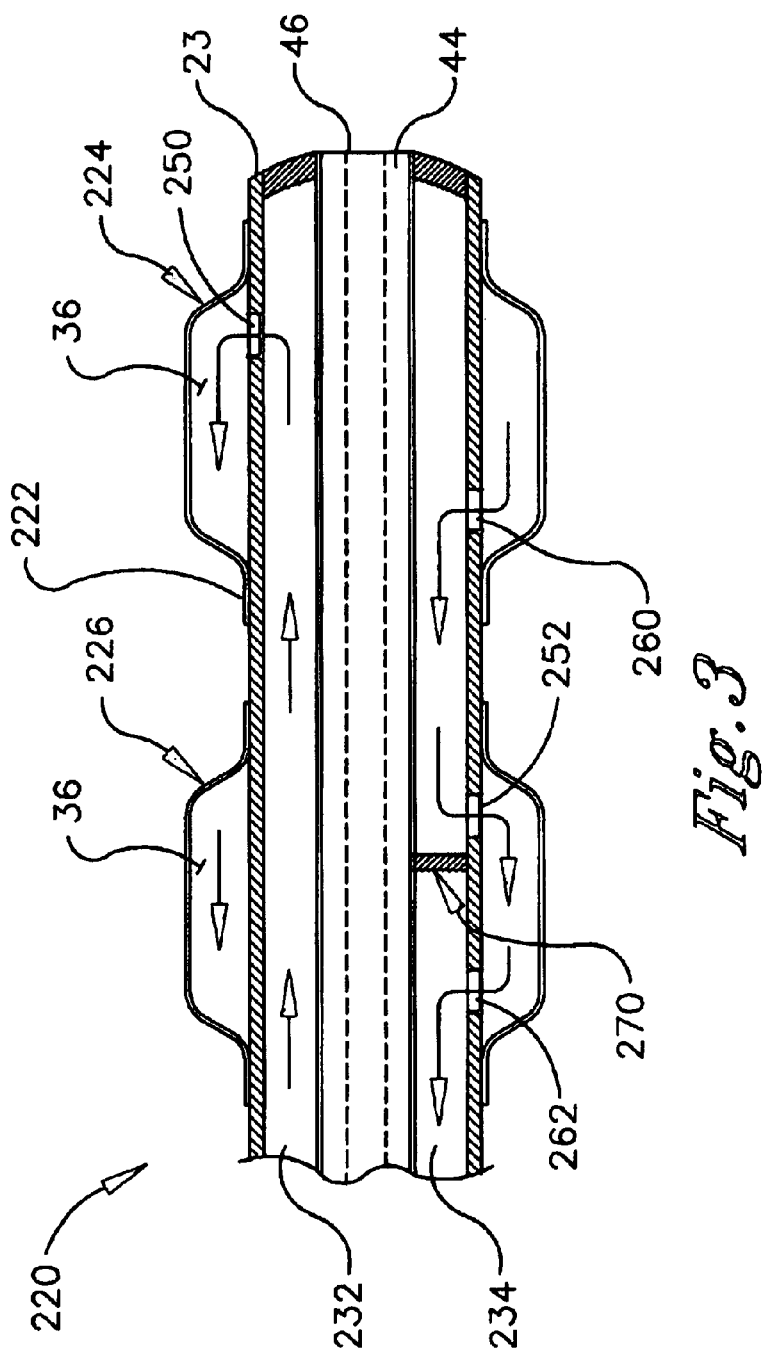

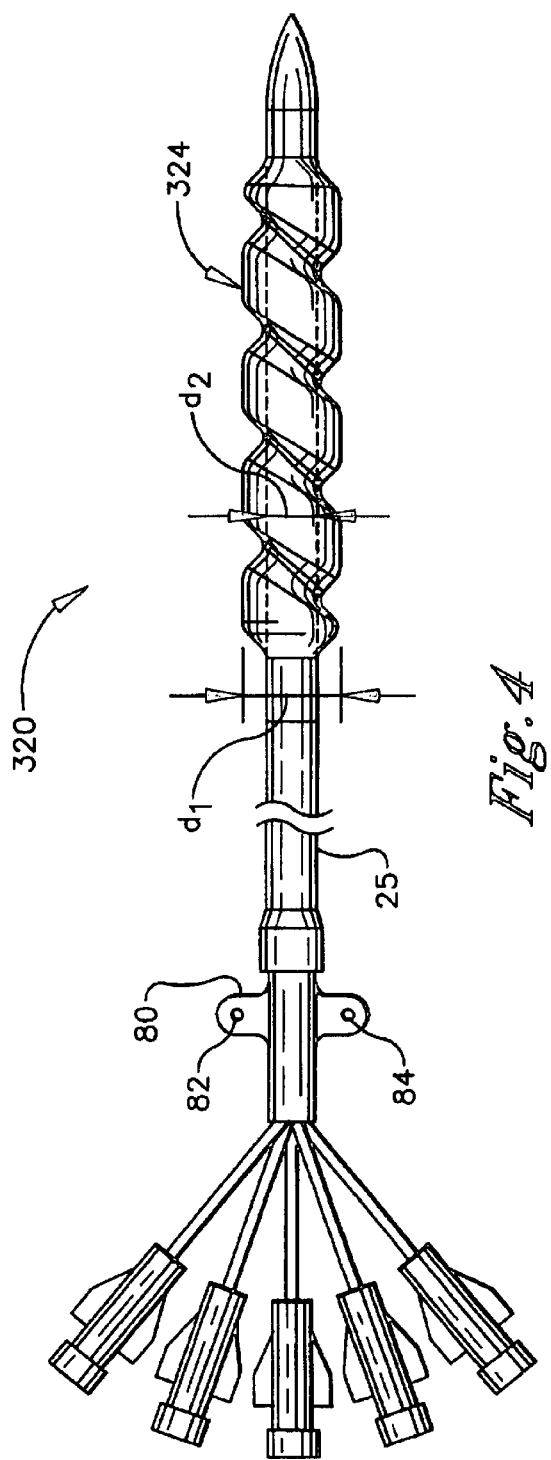

Fig. 11

| LEAD INVESTI-GATOR | YEAR | POPULATION | N | IVC DIA (mm) (MEAN) | IVC DIA (mm) STD DEV |
|---|---|---|---|---|---|
| 1 | 1994 |  | 180 | 18.4 | 1.6 |
| 2 | 1989 | 29 FEM 71 MALE | 100 | 21.9 |  |
| 3 | 1989 | 18 TO 92 YEARS OLD | 100 | 20.9 21.3 |  |
| 4 | 1983 |  | 65 | 20 | 3 |
| 5 | 1994 |  | 11 |  |  |
| 6 | 1992 | 19 YR. OLDS | ? | 20.84 |  |
| 6 | o | 18 YR. OLDS | ? | 20.58 |  |
| 7 | 1996 P. 107 | 11 M:F 18 80 YRS OLD | 50 |  |  |
| 8 | 1990 | NORMAL | 32 |  |  |

Fig.11 cont.

| IVC DIA (mm) MAX | IVC DIA (mm) MIN | IVC LENGTH (mm) (MEAN) | IVC LENGTH (mm) MAX | IVC LENGTH (mm) MIN |
|---|---|---|---|---|
|  |  |  |  |  |
| 34 | 17 |  |  |  |
| 27, 31 | 12, 10 |  |  |  |
| 30 | 13 |  |  |  |
|  |  |  |  |  |
| 36.4 | 20.5 | 225 | 272 | 179 |
| 33.6 | 18 | 206 | 252 | 160 |
|  |  |  |  |  |
|  |  |  |  |  |

*Fig.11 cont.*

| INFRARENAL IVC LENGTH (mm) (MEAN) | INFRARENAL IVC LENGTH (mm) (STD DEV) | INFRARENAL IVC LENGTH (mm) MAX | INFRARENAL IVC LENGTH (mm) MIN |
|---|---|---|---|
| 95.2 | 2.7 | | |
| 96.3 | | 140 | 55 |
| 96 | | 142 | 80.3 |
| | | | |
| | | | |
| | | | |
| | | | |
| | | | |
| | | | |

*Fig.11 cont.*

| LLIAC DIA IVC LENGTH (mm) (MEAN) | LLIAC DIA (mm) (STD. DEV.) | LLIAC DIA DIA (mm) (MAX) | LLIAC DIA (mm) (MIN) |
|---|---|---|---|
| 9.7 | 1.3 | | |
| 13.6 | | 24 | 5 |
| | | | |
| | | | |
| | | | |
| 14.2 | | 18.8 | 9.6 |
| 12.7 | | 17.3 | 8.2 |
| | | | |
| | | | |

Fig.11 cont.

| FEM DIA (mm) (MEAN) | FEM DIA (mm) (STD. DEV.) | FEM DIA (mm) (MAX) | FEM DIA (mm) (MIN) |
|---|---|---|---|
|  |  |  |  |
|  |  |  |  |
|  |  |  |  |
|  |  |  |  |
| 5.3 | 0.9 |  |  |
| 12.6 |  | 16.5 | 8.8 |
| 11.5 |  | 15.3 | 7.7 |
| 11.1 | 1.5 | 13.4 | 7.5 |
| 9.4 |  |  |  |

CENTRAL VENOUS LINE CATHETER HAVING MULTIPLE HEAT EXCHANGE ELEMENTS AND MULTIPLE INFUSION LUMENS

This is a continuation-in-part application of U.S. patent application Ser. No. 09/253,109, filed Feb. 19, 1999, which is incorporated herein by reference.

BACKGROUND OF THE INVENTION

1. Field of the Invention

The field of the present invention is apparatus and methods for producing heat exchange with a body fluid flowing through a body conduit of a patient.

2. Description of Related Art

Catheters such as central venous line catheters are typically used in ICU (intensive care unit) patients, particularly in those patients who have suffered a stroke or other brain traumatic event. Central venous line catheters are typically about 5 to 12 French in size and have a flexible multi-lumen elongated body extending 6 to 12 inches. They may be introduced through the subclavian or jugular veins, or through the femoral vein of the patient, serving to provide the caretaker with easy and convenient access to the patient's central blood supply via the central venous system. In this manner general access to the central blood supply is gained, enabling, for example, delivery of drugs, infusion fluids or nutrition, along with the gathering of patient blood for blood gas analysis and the like.

In certain medical circumstances, such as in the case of a stroke patient or other brain trauma patient, it may be desirable to rapidly reduce the patient's body temperature. For example, fever, which is common in neuro-ICU patients, may exacerbate detrimental effects in the brain. It may be desirable to reduce the body temperature of a patient having a fever to a normal body temperature. In other cases, it is sometimes considered desirable to reduce the patient's body temperature below normal body temperature so that the patient experiences hypothermia. Many advantages of hypothermia are known. By way of example, it has been found desirable to lower the temperature of body tissue in order to reduce the metabolism of the body. This has been particularly desirable in surgical applications where the reduced metabolism has made it possible to more easily accommodate lengthy operative procedures. In cases of stroke and several other pathological conditions, hypothermia also reduces the permeability of the blood/brain barrier. It inhibits release of damaging neurotransmitters and also inhibits calcium-mediated effects. Hypothermia also inhibits brain edema and lowers intracranial pressure.

Conventional therapies to cool a patient include treatment with acetaminophen (Tylenol), cooling blankets, ice water bladder lavages, and ice baths. These approaches to cooling a patient require excessive cooling time and do not provide for precise control of patient cooling.

In other medical situations, it may be desirable to raise the patient's body temperature. For example, a patient may suffer from unintended hypothermis and may need to be warmed to a normothermic temperature, e.g., 98.6° F. These results can be obtained by intravascular heating.

In order to minimize the number of incisions and catheter insertions into the patient's body and cool or heat the patient relatively quickly and in a controlled fashion, an infusion catheter may be configured to include a heat exchange capability.

By supplementing the known functions of a central venous line catheter with the function of cooling or warming the patient's blood, a catheter may take advantage of existing access to the venous system using a single, relatively small incision, reducing the risk of additional complications. The access, typically through the subclavian, jugular or femoral veins, is to the central blood supply, via the central venous system, and is therefore particularly expedient, permitting efficient cooling or warming of a patient. The term central venous system generally relates to the portion of the venous system which returns blood to the right side of the heart, including the inferior and superior vena cava.

An infusion catheter having one or more lumens may be inserted into a blood vessel of a patient to deliver medication, collect blood for analysis, and the like. A separate lumen may be provided for transporting a heat exchange fluid, e.g., cold or hot water or saline. The fluid may circulate via the lumen and through a thin-walled inflated balloon formed on the surface of the catheter. The fluid exchanges heat with the blood in the blood vessel via the thin walls of the balloon. Outside the patient's body, the fluid passes through a cooling or heating system to re-cool or re-heat the fluid. Such a catheter may lower or raise the temperature of the patient's blood and, as described above, may thereby improve the patient's medical condition.

It would be advantageous to provide a central venous catheter with the capability of maximizing cooling or heating of a patient safely and in a controlled manner. The rate of heat transfer depends on such factors as the volumetric flow rates of the blood and the heat exchange fluid, and the temperature difference between the heat exhcanger and the blood. Other factors include the convection heat transfer coefficient of the two fluids involved in the heat exchange, the thermal conductivity and thickness of the barrier between the two fluids, and the residence time of the heat transfer. Increasing the cooling or heating rate may be accomplished by, for example, increasing the size (diameter and/or length) of the balloon, or increasing the temperature difference between the heat exchange fluid and the blood.

Increasing the diameter of the balloon, however, may result in blocking the flow of blood in the blood vessel, and/or may cause thrombosis. Increasing the size of the balloon is further complicated by the fact that the size of blood vessels may vary widely among different patients. A catheter that maximizes heat transfer for a larger patient may be too large for use in a smaller patient, and a catheter that maximizes heat transfer for a smaller patient may not maximize heat transfer in a larger patient. For example, a relatively large balloon, when inflated, may excessively block blood flow through a smaller patient's blood vessel, increasing the risk of thrombosis. Further, a tip of a relatively large catheter designed for a larger patient, if inserted completely into a smaller patient's upper central venous system, may extend into the patient's heart.

Increasing the temperature difference between the heat exchange fluid and the blood excessively may lead to undesireable effects, such as thermal damage to the blood vessel wall. Further, blood has a maximum desirable heating limit because above certain termperatures blood proteins may degenerate and coagulation may occur. This limits the maximum operating temperature of known intravascular catheters.

The rate of heat transfer may also depend partially on the geometry of the heat exchanger. Because the operating temperature of an intravascular catheter is limited, the catheter geometry may take on increased importance to effectuate heat transfer. The flow of the heat exchange fluid inside the balloons may be non-laminar, and the flow of the patient's blood over the balloons may also be non-laminar, such that much of the heat exchange occurs between only portions of the heat exchange fluid and blood that are nearest the balloon surfaces. To promote mixing or disturbance of the flow paths of the heat exchange fluid and the patient's blood, the balloons may be configured in helical (referred to interchangeably herein as "spiral") shapes, or otherwise configured, such that the flow of the heat exchange fluid and the blood is non-laminar, increasing the rate of heat transfer.

It would be advantageous to provide a heat exchange catheter that maximizes intravascular cooling and heating without comprising physiological conditions, and facilitates access to the patient's blood stream, thereby overcoming one or more problems associated with the related art.

BRIEF SUMMARY OF THE INVENTION

The present invention is directed to a heat exchange catheter and method for its use. A heat exchange element or elements is combined with an infusion lumen or lumens to provide efficient cooling (and/or heating) and access to the patient's blood steam.

In a first separate aspect of the invention, a heat exchange catheter comprises a generally tubular elongated body defining an inflow lumen, an outflow lumen, and at least one infusion lumen. The inflow and outflow lumens circulate heat exchange fluid within a plurality of heat exchange elements disposed about a distal, implantable portion of the catheter; while the infusion lumen serves to provide access to the central blood supply of the patient.

In a second separate aspect of the invention, a heat exchange catheter has a cross-sectional size such that no more than approximately 30% to 75% of the cross-section of a blood vessel in which the catheter is inserted is blocked by the catheter.

In a third separate aspect of the invention, one or more heat exchange elements is disposed over a particular length of the elongated body such that the heat exchange elements the maximize heat transfer rate without harming the patient.

In a fourth separate aspect of the invention, a heat exchange catheter may be inserted into a patient's central venous system through the patient's femoral vein.

In a fifth separate aspect of the invention, a heat exchange catheter is provided with multiple infusion lumens (preferably three to five infusion lumens) with infusion ducts separated along the catheter at spaced intervals, such that the catheter may be used to simultaneously introduce various fluids, such as medications, into the patient at different points in the patient's blood stream, so as to avoid mixing incompatible fluids in excessive concentrations.

In a sixth separate aspect of the invention, a heat exchange catheter is provided with multiple balloons (preferably three or four balloons) that are spaced along the elongated body to provide controlled and balanced heat transfer, with a gap between balloons to provide the catheter with flexibility.

In a seventh separate aspect of the invention, a heat exchange catheter is provided with gaps between multiple balloons, so that an infusion duct may be disposed in each gap.

In an eighth separate aspect of the present invention, it is contemplated that combinations of the foregoing separate aspects may be incorporated into a single embodiment.

Therefore, it is an object of the present invention to provide an improved heat exchange catheter and a method for its use. Other and further objects and advantages will appear hereafter.

BRIEF DESCRIPTION OF THE DRAWINGS

FIG. 3 is a schematic sectional view of a distal portion of another embodiment of an intravenous catheter;

FIG. 4 is a schematic side elevational view of another embodiment of an intravenous catheter;

FIG. 11 is a table of data regarding blood vessel sizes of samplings of persons.

DETAILED DESCRIPTION OF THE INVENTION

Figures 1, 1A:
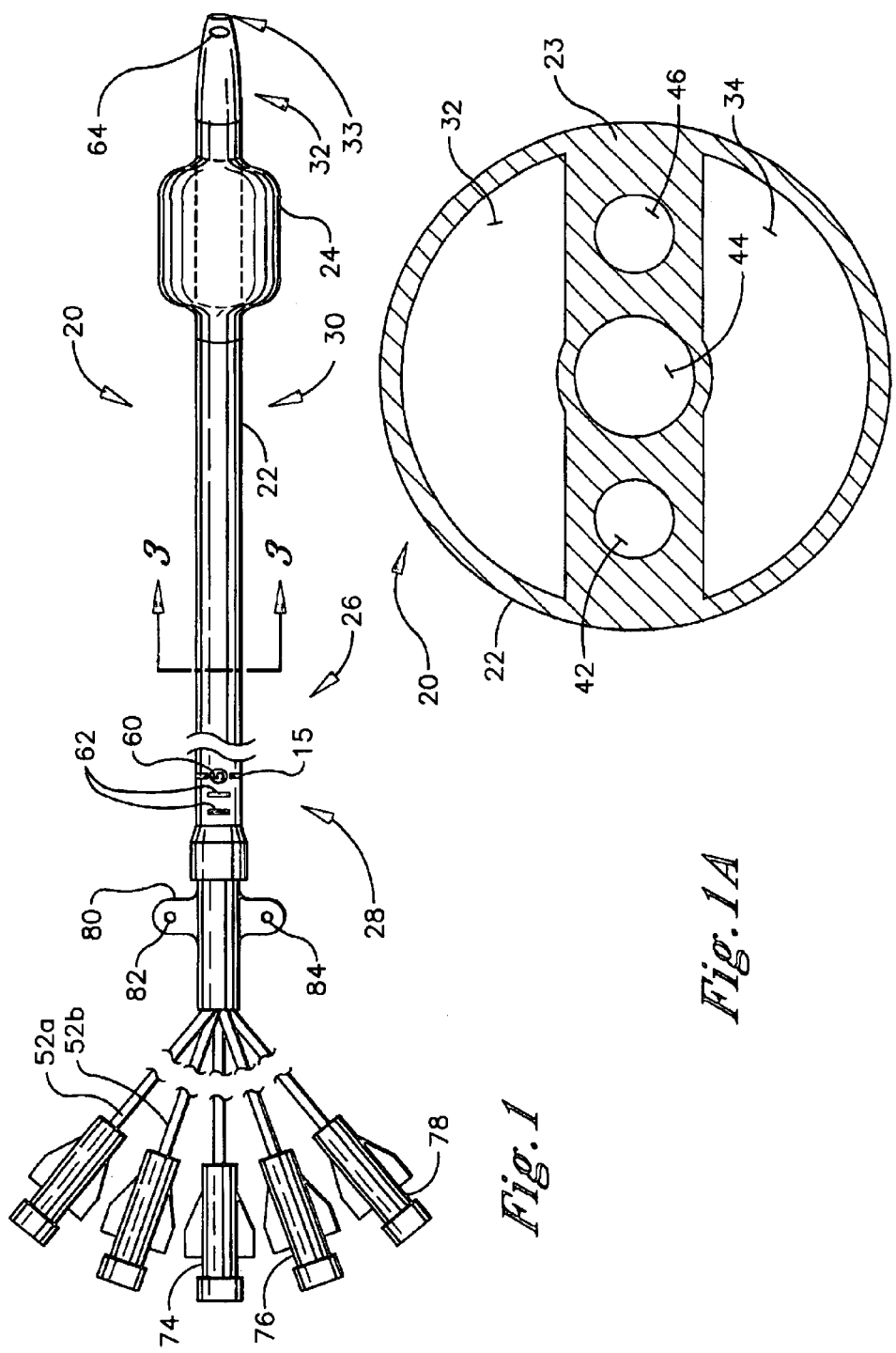
FIG. 1 is a schematic side elevational view of an intravenous catheter.
FIG. 1A is a cross-sectional view of the intravenous catheter of FIG. 1.

The preferred embodiments will be described with reference to drawing figures, wherein like reference numerals are applied to like elements.

U.S. Pat. Nos. 6,146,411, 6,126,684, and 6,165,207 each of which is hereby incorporated by reference, disclose systems employing catheters that may be inserted into the body of a patient to exchange heat with the blood supply of the patient.

FIGS. 1 and 1A depict one embodiment of an intravascular catheter 20 adapted to exchange heat with a body fluid flowing through a body conduit of a patient. The catheter 20 comprises an elongated body 22 having a substantially tubular configuration, having a proximal portion 26 with a proximal end 28, and having a distal portion 30 with a distal end 32. When operatively disposed, the distal end 32 is disposed within the patient's body, and the proximal end 28 is disposed outside of the patient's body.

One or more depth markings 60 62 may be disposed on the elongated body 22 to indicate the length of a portion of the catheter 20 that is intubated into the patient. Preferably, the depth markings 60 62 are disposed at least on the proximal portion 26 of the elongated body 22 so that they are visible when the catheter 20 is intubated into the patient. The markings 60 62 preferably indicate a length of the catheter 20 measured from each marking 60 62 to the distal tip 33 of the catheter 20 and may be disposed at spaced intervals, such as one-centimeter intervals. Each marking 60 62 may comprise any symbol that may be understood to represent a length or relative length or degree of intubation. One marking 60 is shown to comprise a numeral indicative of length (in centimeters, for example) from the marking 60 to the distal tip 33 of the catheter. Other markings 62 may comprise dots, lines, hash marks or other marks.

The elongated body 22 may also include a distal indicator 64 that indicates the position of the distal end 32 or distal tip 33 of the elongated body 22. The distal indicator 64 preferably is disposed near the distal tip 33 of the elongated body 22. The position of the distal indicator 64 inside the patient preferably may be determined using conventional medical technology, such as with X-ray technology. Information regarding the position of the distal end 32 or distal tip 33 of the elongated body 22 may aid proper placement of the catheter 20, so that the catheter 20 is inserted to a degree that maximizes the heat transfer rate without compromising physiological effects.

Referring to FIG. 1A, which is a cross-sectional view of the catheter 20 of FIG. 1, the elongated body 22 comprises an inflow lumen 32, an outflow lumen 34, and three infusion lumens 42 44 46. The infusion lumens 42 44 46 may serve a multiplicity of functions, including infusion of drugs such as chemotherapy, fluids and nutrition, guidewire support, access to syringes for sampling, and accommodation of various sensors, such as thermistors to monitor the patient, thus generally providing access to the central blood supply as dictated by the particular application. Each infusion lumen 42 44 46 preferably has an infusion duct (infusion ducts are further described in connection with FIGS. 8–10) for providing fluid communication between the infusion lumen 42 44 46 and the body conduit in which the catheter 20 is intubated. Additionally, an infusion lumen such as the central infusion lumen 44 may be made of a different diameter than the other infusion lumens 42 46 in order to better support a guidewire for instance. While the catheter 20 depicted in FIG. 1 has three infusion lumens 42 44 46, and while the preferred number of infusion lumens is three, four, or five infusion lumens, other numbers of infusion lumens are contemplated and may be suitable depending on the particular application.

The catheter 20 preferably is formed of a polymer material 23 that defines the various lumens 32, 34, 42, 44 and 46. A preferred material 23 is polyurethane, although other materials, such as nylon, polyethylene, PEBAX, PVC, Tygon® or the like can also be used. Considerations in selecting the appropriate material 23 include biocompatibility, flexibility, temperature change compatibility, and resistance to buckling.

At least one heat exchange element 24, such as fluid-carrying inflatable balloon, extends at least partially along the implantable, distal portion 30 of the elongated body 22. For ease of description, this embodiment is shown to have only one heat exchange element 24. Preferably, however, a catheter has two, three, or four heat exchange elements, as will be described below in connection with other embodiments. Further, a catheter may have more than four heat exchange elements.

Heat exchange fluid (not shown) flows within the catheter 20 to heat or cool a patient. The heat exchange fluid is remotely cooled or heated outside of the catheter 20, such as by a temperature control system (not shown), and is conveyed between the catheter 20 and, for example, a temperature control system, via an inlet tube 52a and an outlet tube 52b. External access to the infusion lumens 42 44 46 is supplied by infusion lumen fittings 74 76 78.

Figure 2:
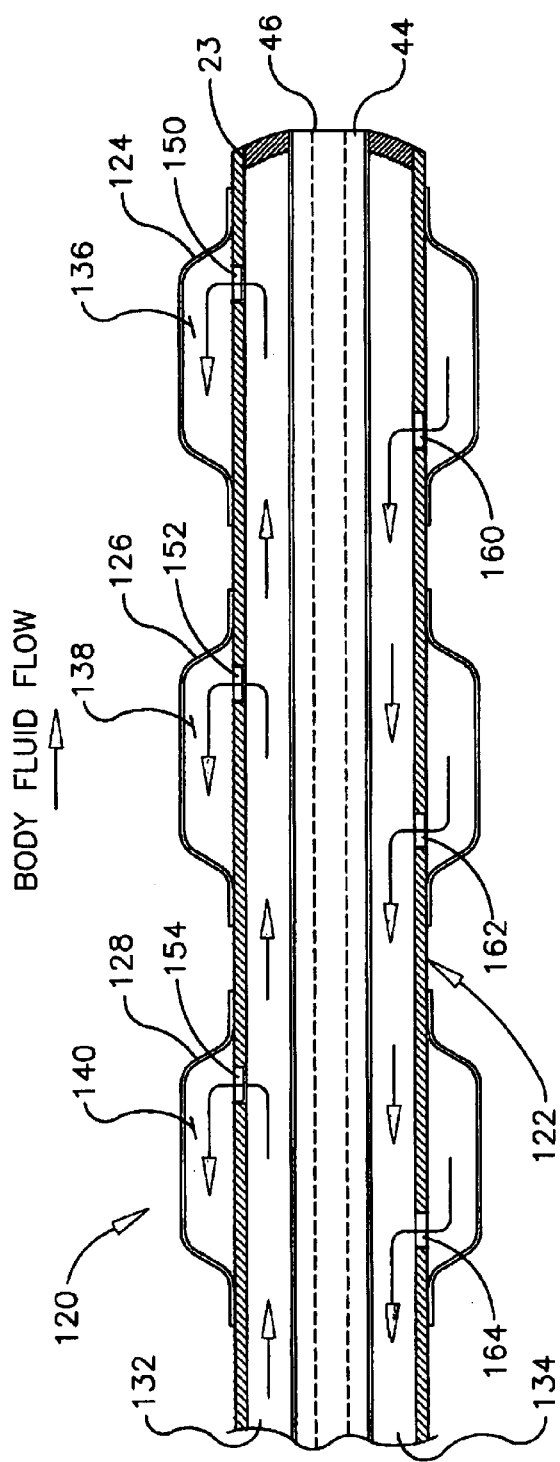
FIG. 2 is a schematic sectional view of a distal portion of an embodiment of an intravenous catheter.

FIG. 2 depicts a distal portion of a catheter 120 having three heat exchange elements 124 126 128. Although this embodiment has three heat exchange elements 124 126 128, the principles described herein apply to catheters having any number of heat exchange elements.

One of the advantages of a multiple heat exchange element configuration is that the flow and temperature of heat exchange fluid that circulates in the catheter can be more easily controlled along the catheter such that a more even and balanced transfer of heat can be achieved. Further, multiple heat exchange elements may provide an increased surface area relative to embodiments having a single heat exchange element. Another advantage of a multiple heat exchange elements design is the ability of the catheter to bend and flex when placed in a curved vasculature.

Each heat exchange element 124 126 128 defines with the elongated body 122 a cavity 136 138 140. Heat exchange fluid (as indicated by the arrows in FIG. 2) is circulated through the heat exchange elements 124 126 128 via the inflow lumen 132 and the outflow lumen 134.

The particular heat exchange fluid selected is preferably biocompatible to avoid harm to the patient in the event of inadvertent rupture. Candidate materials include sterile saline water and carbon dioxide gas, although other fluids having suitable viscosity, heat exchange and material compatibility characteristics can also be used. While less desired because it is not biocompatible, freon can alternatively be used.

The fluid may be either relatively cold or relatively warm, depending on whether patient cooling or heating is desired. While in the cavity 136 138 140 of the heat exchange element 124 126 128, the heat exchange fluid serves to provide a cold or warm fluid on an inner surface of each heat exchange element 124 126 128. With a body fluid, such as blood, flowing exteriorly of the heat exchange element 124 126 128, heat transfer occurs across the heat exchange element 124 126 128, effectively cooling or heating the body of the patient. The temperature of the heat exchange fluid is remotely controlled in order to achieve a desired patient target temperature or temperature range.

The inflow lumen 132 serves as an inflow channel supplying the heat exchange elements 124 126 128 with heat exchange fluid which is circulated through the catheter 20, while the outflow lumen 134 serves as an outflow channel returning the heat exchange fluid from the heat exchange elements 124 126 128 to the catheter 120.

Each of the heat exchange elements 124 126 128, each of which preferably comprises a balloon, may be formed from a piece of flexible sheet material or extruded tubing formed into a molded balloon of the desired shape and size and then bound or otherwise fixed to the elongated body 122 to form each cavity 136 138 140. In one embodiment, each heat exchange element 124 126 128 is made of urethane, nylon, or PET and is thin-walled, i.e., has a wall thickness of less than three mils, and more preferably less than one and one-half mils.

The heat exchange elements 124 126 128 alternately may be made of metal such as steel, and may assume an appropriate configuration, such as an accordion-like configuration. Further, each heat exchange element 124 126 128 preferably is coated with an antimicrobial substance, as well as an anticlot substance, such as heparin.

Each balloon preferably is inflatable from a flattened configuration, wherein the balloon lies substantially flush with the elongated body 122 of the catheter 120, to an operational configuration, wherein the heat exchange fluid inflates each balloon. The flattened configuration facilitates insertion of the catheter 120 into the body of a patient.

As shown in FIG. 2, the elongated body 22 includes an inflow duct 150 152 154 and an outflow duct 160 162 164 for each heat exchange element 124 126 128. Each inflow duct 150 152 154 is in fluid communication with the inflow lumen 132. Each outflow duct 160 162 164 is in fluid communication with the outflow lumen 134. Heat exchange fluid introduced into the inflow lumen 132 enters a cavity 136 138 140 of each heat exchange element 124 126 128 through an inflow duct 150 152 154, flows through the heat exchange element 124 126 128, exits the heat exchange element 124 126 128 through an outflow duct 160 162 164, and flows through the outflow lumen 134 toward the proximal end of the catheter 120.

The inflow duct 150 152 154 of each heat exchange element 124 126 128 preferably is positioned distally of the corresponding outflow duct 160 162 164 to provide countercurrent flow, which facilitates the maximum heat exchange between the heat exchange fluid and the body fluid, e.g., blood.

The amount of flow within each of the heat exchange elements 124 126 128 (which are preferably balloons in this case) may be controlled by the size of the inflow ducts 150 152 154 and outflow ducts 160 162 164. In this embodiment, this flow control is provided by the inflow ducts 150 152 154; the outflow ducts 160 162 164 are sized larger than their respective inflow ducts 150 152 154 so that they offer little resistance to flow.

Further, the inflow ducts 150 152 154 are progressively smaller from the distal end to the proximal end. The inflow duct 150 is larger than the inflow duct 152 which is in turn larger than the inflow duct 154. As a result, the resistance to the flow of heat exchange fluid in the most distal balloon is less than that in the most proximal balloon. This helps distribute the coolest or warmest heat exchange fluid equally among all of the balloons regardless of their position along the elongated body 122. Further information regarding the positions and relative sizes of inflow ducts and outflow ducts is disclosed in U.S. Pat. No. 6,126,684.

In the embodiment depicted in FIG. 2, the heat exchange fluid flows in parallel flow paths, such that fluid circulating through one of the balloons returns to the proximal end of the catheter without circulating through any other balloon. Using parallel flow paths, substantially equal heat exchange capacity is available in each balloon.

In other embodiments, heat exchange fluid may flow in a serial flow path, such that fluid circulating through one of the balloons flows into another balloon before returning to the proximal end of the catheter. An embodiment having a serial flow path is depicted in FIG. 3. Although FIG. 3 depicts an embodiment having two balloons, the principles set forth herein in connection with FIG. 3 may apply to catheters having any number of balloons.

As shown in FIG. 3, a serial flow path may be provided by, for example, arranging the inflow ducts 250 252 such that only one inflow duct 250 is in direct fluid communication with the inflow lumen 232, and such that all other inflow ducts 252 are in direct fluid communication with the outflow lumen 234. Fluid flow through the outflow lumen 234 may be blocked by an obstruction 270 such that, for example, fluid flows into the outflow lumen 234 from a first balloon 224 through a first outflow duct 260, flows in a proximal direction through the outflow lumen 234 toward a second inflow duct 252, and flows through the second inflow duct 252 into a second balloon 226. The obstruction 270 may direct fluid into the second inflow duct 252 by blocking fluid flow through the outflow lumen 234 proximal of the second inflow duct 252.

In any of the embodiments, various balloon shapes may be employed, including but not limited to helical, cylindrical, and fluted shapes. The particular shape selected depends on the application and the desired heat exchange and other characteristics. Heat exchange is enhanced when either, or both, the body fluid or the heat exchange fluid is provided with well mixed flow. Mixing can be enhanced by providing irregular surfaces next to which either of these fluids flow. Further information regarding mixing is disclosed in U.S. Pat. No. 6,126,684.

To enhance mixing of the blood and heat exchange fluid, a catheter preferably has one or more balloons having a helical shape. A helical balloon enhances mixing of the heat exchange fluid inside the balloon and increases residence time of the heat exchange fluid inside the balloon, increasing the heat exchange capacity of the balloon. The helical shape is further believed to cause mixing of blood flowing past the helical-shaped balloon in the venous system, improving heat transfer by increasing the amount of blood exposed to the surface of the balloon.

Figure 5A:
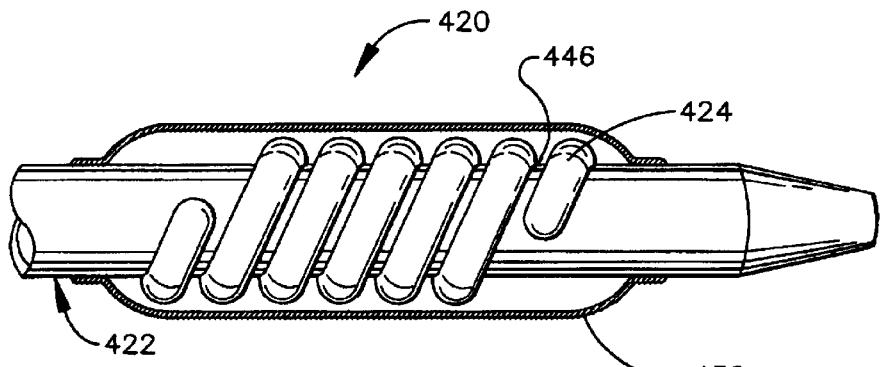
FIGS. 5A, 5B, and 5C are schematic side elevational views of distal portions of different embodiments of an intravenous catheter having a helical heat exchange element.
Figure 5B:
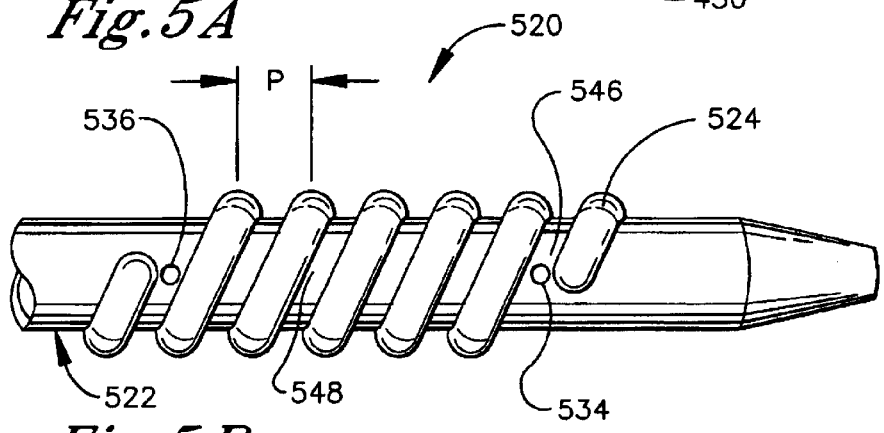
Figure 5C:
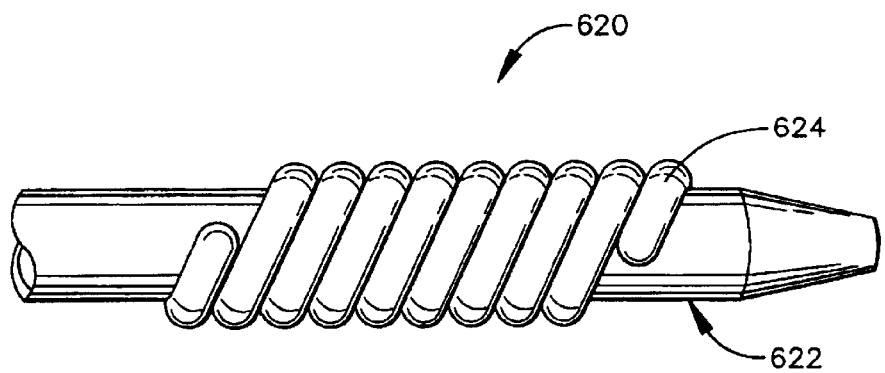

FIG. 4 depicts a catheter 320 having one balloon 324 with a helical shape. FIGS. 5A, 5B, and 5C distal portions of catheters 420 520 620 having one helical balloon 424 524 624. Each of the helical balloons 424 524 624 turns or wraps in a spiral or helix about an elongated body 422 522 622 of a catheter 420 520 620. Each of the balloons 424 524 624 has a pitch that is indicative of a distance between turns of the balloon 424 524 624. An example of a distance between turns is indicated by "p" in FIG. 5B. A preferred distance between each turn of the helix is 7.5 to 18 mm.

Referring to FIG. 5A, a covering 450 may surround portions of one or more balloons 424 to prevent coagulum from forming in the gap 446 between the turns of a balloon 424 or to minimize turbulence and shear which can be damaging to blood. The covering preferably 450 comprises an elastomeric material.

Figure 6:
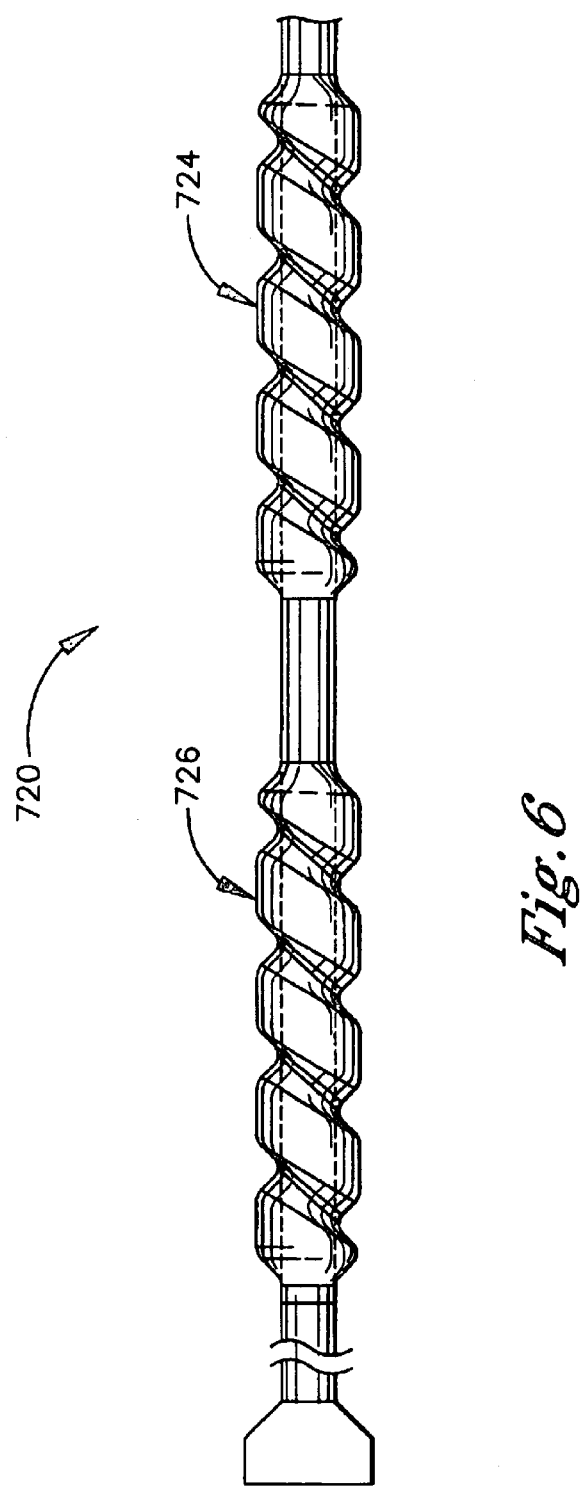
FIG. 6 is a schematic side elevational view of an embodiment of an intravenous catheter having two helical heat exchange elements.

A catheter may have more than one helical balloon. FIG. 6 depicts a catheter 720 having two helical balloons 724 726. Each helical balloon 724 726 may have either a fixed pitch, such that the distance between turns of the balloon 724 726 is substantially constant over the length of the balloon 724 726. Alternately, each helical balloon 724 726 may have a variable pitch, such that the distance between turns of the balloon 724 726 varies over the length of the balloon 724 726. Further, the helical balloons 724 726 may have the same or different pitches.

Figure 7:
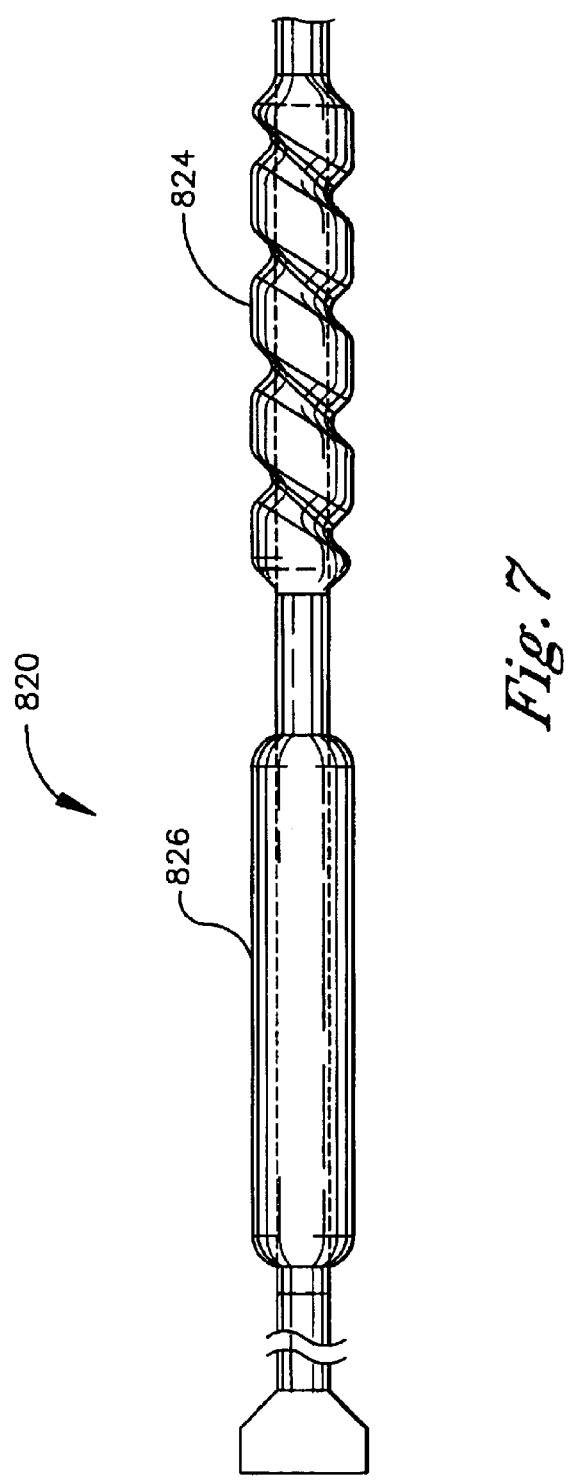
FIG. 7 is a schematic side elevational view of an embodiment of an intravenous catheter having one helical heat exchange element and one straight heat exchange element.

A catheter may have balloons of different shapes. As depicted in FIG. 7, for example, a catheter 820 may have a combination of one or more helical balloons 824 and one or more straight balloons 826.

A catheter preferably has a size (e.g., length and diameter and/or cross-sectional area) that maximizes the heat transfer rate without causing harmful physiological effects. It is believed that in at least some blood vessels, flow of blood through the vessel begins to be reduced when approximately 50% of the blood vessel cross section is blocked. To maintain blood flow, the cross-sectional size (e.g., diameter and/or area) of the balloon, in combination with the cross-sectional size of the elongated body, preferably is no more than approximately 30% to 75% of the cross-sectional size of the blood vessel in which the balloon is inserted. This range may be modified to provide a suitable safety margin.

The preferred size of a catheter will vary with the size of each patient's vasculature. Data regarding blood vessel size for a sampling of persons is compiled in FIG. 11. Using the maximum and minimum diameters and lengths, preferred diameters and lengths for each balloon were calculated so that no more than 30% to 75% of the vessel cross-section would be blocked by each balloon.

In the case of a catheter having three balloons, it was determined that the preferred diameters (indicated by way of example in FIG. 4 by "$d_1$") of each balloon, from a distal-most to a proximal-most balloon, are approximately 5 to 9 mm, approximately 5 to 9 mm, and approximately 4 to 6 mm. Based on the data in FIG. 11, it is believed that such a three-balloon catheter would be especially suitable for use in the smallest 50% of patients.

Based on the maximum blood vessel dimensions in FIG. 11, it is believed that a four-balloon catheter would be suitable for use in the largest 50% of patients. For a catheter having four balloons, the preferred diameters, $d_1$, would be, from a distal-most to a proximal-most balloon, approximately 8 to 12 mm, approximately 8 to 12 mm, approximately 5 to 9 mm, and approximately 4 to 6 mm.

Referring to FIG. 4 by way of example, the cross-sectional size, $d_2$, of the elongated body of the catheter defines an inner dimension of the balloons. The balloons typically have a significantly larger diameter, $d_1$, than the elongated body's diameter, $d_2$. For example, it is contemplated that in some applications the diameter of the inflated balloon, $d_1$, will be more than three times the diameter of elongated body, $d_2$. It may be desirable in some embodiments to increase the relative diameter of the elongated body in order to facilitate flow of the heat exchange fluid. Further information regarding such embodiments is disclosed in U.S. Pat. No. 6,126,684.

The length of each balloon also influences the heat transfer rate for each balloon. To maximize the heat transfer rate, the balloons preferably extend along substantially the entire length of the portion of the catheter that is intubated in the patient. Typically, this length is about 15 to 25 cm, as indicated by FIG. 11. The preferable length of each balloon will depend on the number of balloons used as well as the intubated length. For example, if the catheter has four balloons and is used in a relatively large patient, each balloon preferably has a length of approximately 58 mm. If the catheter has three balloons and is used in a relatively small patient, each balloon preferably has a length of approximately 58 mm. Different balloon lengths may be suitable in catheters using different numbers of balloons or used with patients of different sizes.

As described above, a catheter preferably has one or more infusion ducts to allow fluid communication between one or more infusion lumens and the patient's body fluid. The infusion ducts preferably are located in areas of the elongated body that are not covered by a heat exchange element so that the infusion ducts need not fluidly communicate through the heat exchange element. Referring to FIG. 5B by way of example, infusion ducts 534 536 may be disposed in gaps 546 548 between turns of a single helical balloon 524.

In catheters having multiple heat exchange elements, the heat exchange elements are preferably spaced apart to define one or more gaps where the elongated body is exposed. Infusion ducts may be located in such gaps, and also may be located adjacent to a single heat exchange element, such as distal of a distal-most balloon, or proximal of a proximal-most balloon. An infusion duct may also be disposed at a distal tip of the catheter or disposed near the distal tip. Further, infusion ducts may be spaced at any combination of locations.

Figure 8:
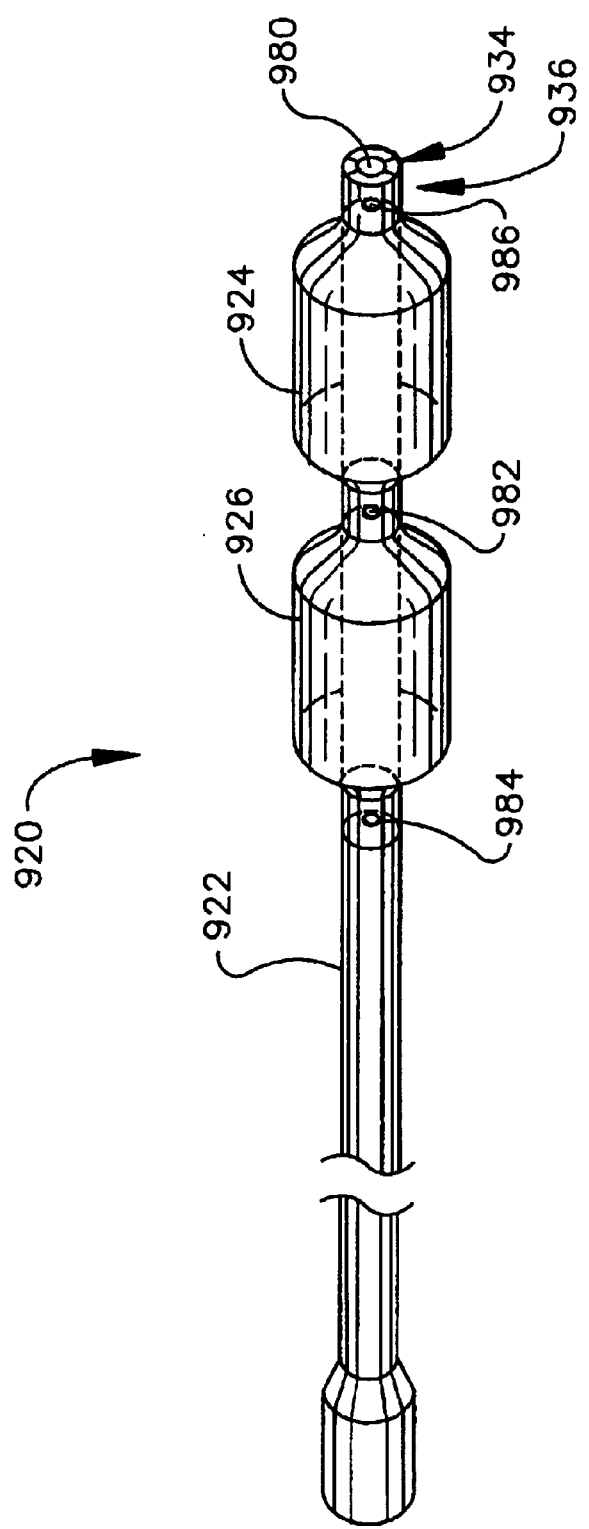
FIG. 8 is a schematic side elevational view of an embodiment of an intravenous catheter having two heat exchange elements and multiple infusion ducts.

For example, as depicted in FIG. 8, a catheter 920 having two balloons 924 926 disposed about the elongated body 922 may have a first infusion duct 980 disposed at a distal tip 934 of the catheter 920, may have a second infusion duct 982 disposed in a gap between the two balloons 924 926, may have a third infusion duct 984 disposed proximal of the balloon 926, and/or may have a fourth infusion duct 986 disposed in a longitudinal side of the catheter 920 near a distal end 936 and between a balloon 924 and the first infusion duct 980. The catheter 920 may have one, all, or any combination of the above-described infusion ducts 980 982 984 986, and may have infusion ducts in other locations as well.

Figure 9:
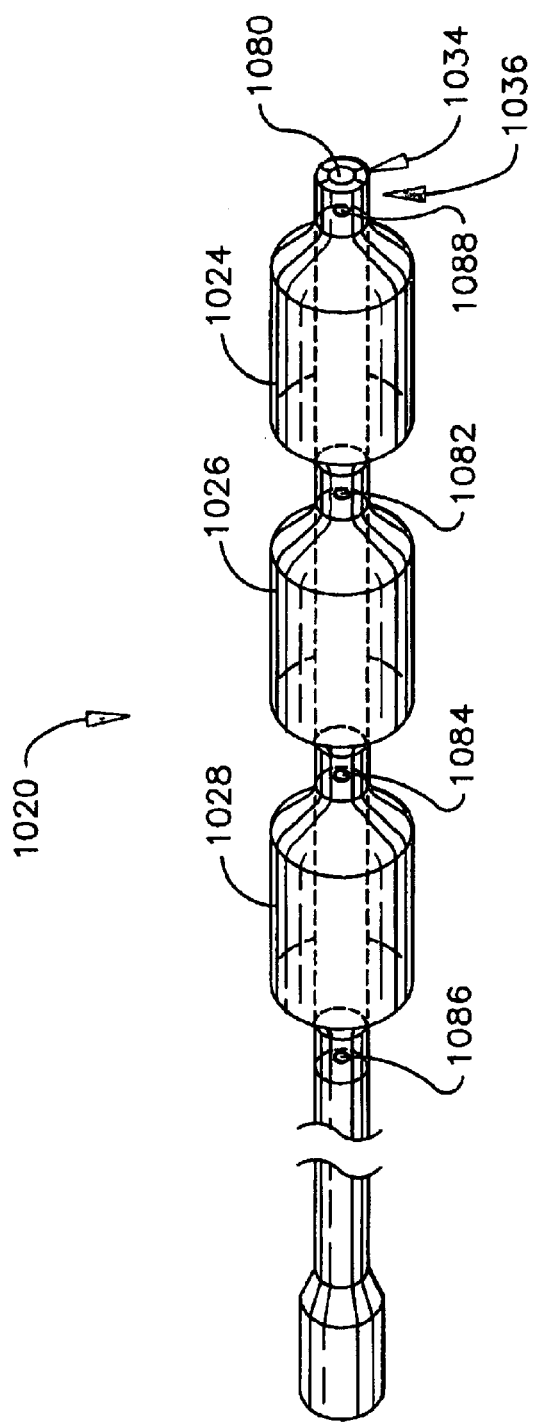
FIG. 9 is a schematic side elevational view of an embodiment of an intravenous catheter having three heat exchange elements and multiple infusion ducts.

As an additional example, a catheter 1020 having three balloons 1024 1026 1028, as depicted in FIG. 9, may have a first infusion duct 1080 disposed at a distal tip 1034 of the catheter 1020, may have a second infusion duct 1082 disposed in a gap between two of the balloons 1024 1026, may have a third infusion duct 1084 disposed in a gap between two other of the balloons 1026 1028, may have a fourth infusion duct 1086 disposed proximal of the balloon 1028, and/or may have a fifth infusion duct 1088 disposed in a longitudinal side of the catheter 1020 near a distal end 1036 and between a balloon 1024 and the first infusion duct 1080. The catheter 1020 may have one, all, or any combination of the above-described infusion ducts 1080 1082 1084 1086 1088, and may have infusion ducts in other locations as well.

Figure 10:
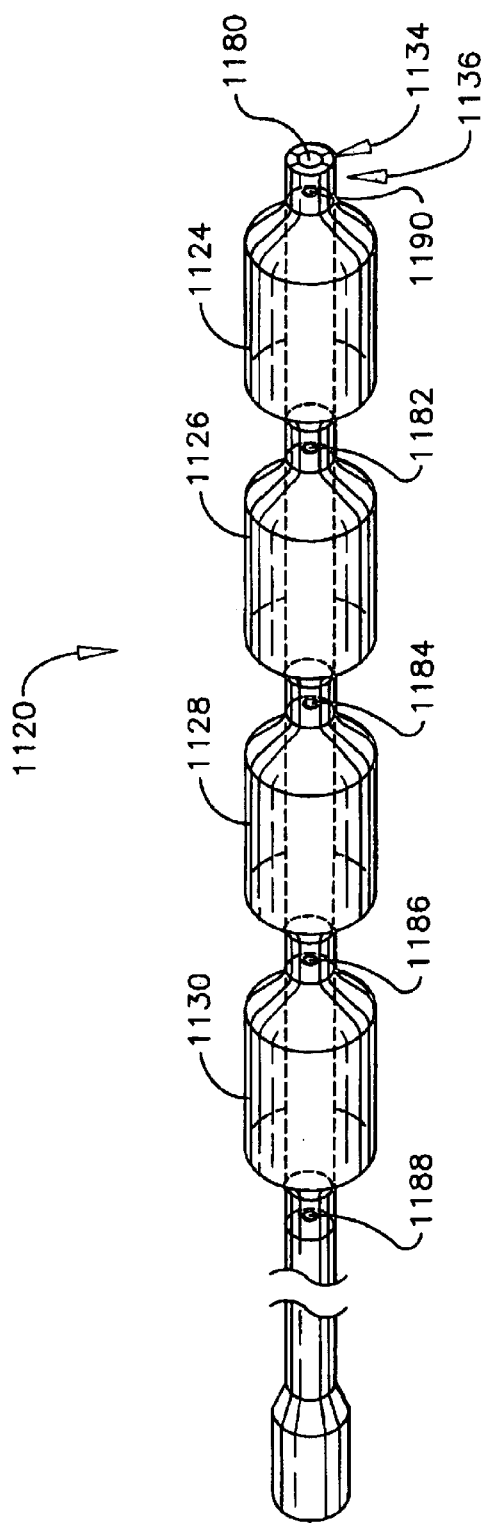
FIG. 10 is a schematic side elevational view of an embodiment of an intravenous catheter having four heat exchange elements and multiple infusion ducts.

As a further example, a catheter 1120 having four balloons 1124 1126 1128 1130, as depicted in FIG. 10, may have a first infusion duct 1180 disposed at a distal tip 1134 of the catheter 1120, may have a second infusion duct 1182 disposed in a gap between two of the balloons 1124 1126, may have a third infusion duct 1184 disposed in a gap between two other of the balloons 1126 1128, may have a fourth infusion duct 1186 disposed in a gap between two other of the balloons 1128 1130, may have a fifth infusion duct 1188 disposed proximal of the balloon 1128, and/or may have a sixth infusion duct 1190 disposed in a longitudinal side of the catheter 1120 near a distal end 1136 and between a balloon 1124 and the first infusion duct 1180. The catheter 1120 may have one, all, or any combination of the above-described infusion ducts 1180 1182 1184 1186 1188 1190, and may have infusion ducts in other locations as well.

Providing multiple infusion ducts that are spaced apart on a catheter allows, for example, the simultaneously delivery different medications to the patient at different locations in the patient's bloodstream, which may be especially desirable where mixing of the medications in relatively high concentrations is desired to be avoided.

Although a heat exchange element may comprise a balloon, the heat exchange element alternately may have a different configuration, such as an array of flexible hollow fibers through which the heat exchange fluid is circulated. Further information regarding hollow fibers and catheter systems having hollow fibers is disclosed in U.S. Pat. No. 6,165,207, which is hereby incorporated by reference as if fully set forth herein.

Referring to FIG. 1, the catheter 20 preferably includes an anchor configured for affixing the catheter 20 to the patient. As shown in FIG. 1, the anchor may comprise a suture fitting 80. The suture fitting 80 can be made integrally with the catheter 20, or it can be made as a separate plastic fitting and engaged with the catheter 20. The suture fitting 80 includes two eyes 82, 84 through which sutures can be inserted and engaged with the patient or with a bandage or tape or other structure that is engaged with the patient. An anchor may be especially desirable in cases in which the catheter is intubated for an extended period.

In accordance with a preferred method, the catheter-may be inserted percutaneously through a puncture or surgical cut near the groin. Following this initial introduction, the catheter may be inserted into the femoral and iliac veins, and the inferior vena cava (IVC), of a patient. The catheter is preferably inserted into blood vessels of the lower central venous system, such as the femoral and iliac veins and the inferior vena cava (IVC) because the volume of the lower central venous system is greater than that of the upper central venous system (jugular or subclavian, innominate, and superior vena cava), allowing a larger catheter (in both length and cross-sectional size) to be used. Alternately, however, the catheter systems disclosed herein may be used in the upper central venous system.

Prior to intubation, the size (e.g., cross-section and/or length) of the body conduit in which the catheter is to be intubated may be measured, and a catheter may be selected based on the size of the body conduit, so that the catheter maximizes the heat transfer rate without deleterious physiological effects to the patient.

The heat exchange relationship between the catheter and the central venous system of the patient may be maintained for a prolonged duration—for example, from about one hour to about twenty-nine days.

Further, the catheter systems disclosed herein may be used in connection with systems for treating cardiac arrest that are disclosed in U.S. Pat. No. 6,149,670, which is hereby incorporated by reference as if fully set forth herein.

While the present invention has been described in terms of the preferred embodiments, other variations which are within the scope of the invention as defined in the claims will be apparent to those skilled in the art.

What is claimed is:

1. An intra-vascular catheter adapted to exchange heat with a body fluid flowing through a body conduit of a patient, comprising:
    a generally tubular elongated body having a proximal portion with a proximal end and a distal portion with a distal end;
    an inflow lumen extending between the proximal portion and the distal portion of the elongated body;
    an outflow lumen extending between the proximal portion and the distal portion of the elongated body;
    at least one infusion lumen extending between the proximal portion and the distal portion of the elongated body;
    at least one inflow duct in fluid communication with the inflow lumen and disposed on the distal portion of the elongated body;
    at least one outflow duct in fluid communication with the outflow lumen and disposed on the distal portion of the elongated body;
    at least one infusion duct in fluid communication with the infusion lumen and disposed on the distal portion of the elongated body;
    at least one heat exchange element for effecting heat exchange with the body fluid in the body conduit, wherein the at least one heat exchange element extends at least partially along the distal portion of the elongated body, fluidly communicates with the inflow duct through which heat exchange fluid may enter the heat exchange element, and fluidly communicates with the outflow lumen through the outflow duct, such that a heat exchange fluid introduced into the input lumen will enter the at least one heat exchange element through the inflow duct and will exit the at least one heat exchange element through the outflow duct:
    a plurality of said infusion lumens, each infusion lumen extending between the proximal portion and the distal portion of the elongated body;
    a plurality of said inflow ducts, each inflow duct being disposed on the distal portion of the elongated body, wherein heat exchange fluid may flow into a heat exchange element through one of said plurality of inflow ducts;
    a plurality of said outflow ducts, each outflow duct being in fluid communication with the outflow lumen and disposed on the distal portion of the elongated body;
    a plurality of said infusion ducts, each being in fluid communication with one of said plurality of infusion lumens; and
    a plurality of said heat exchange elements, wherein heat exchange fluid may enter each of said heat exchange elements through one of said plurality of inflow ducts, and wherein each heat exchange element is in fluid communication with the outflow lumen through one of said plurality of outflow ducts.

2. The catheter of claim 1, wherein said plurality of inflow ducts includes a first inflow duct and a second inflow duct, said plurality of outflow ducts includes a first outflow duct and a second outflow duct, and said plurality of heat exchange elements includes a first balloon defining with the elongated body a first internal cavity, wherein the first internal cavity is in fluid communication with the inflow lumen through the first inflow duct, and is in fluid communication with the outflow lumen through the first outflow duct, and a second balloon defining with the elongated body a second internal cavity, wherein beat exchange fluid may enter the second internal cavity through the second inflow duct, and wherein the second internal cavity is in fluid communication with the outflow lumen through the second outflow duct.

3. The catheter of claim 2, wherein the first balloon has a diameter of approximately 5 to 9 mm, and wherein the second balloon has a diameter of approximately 4 to 6 mm.

4. The heat exchange catheter of claim 2, wherein the first balloon is disposed about the elongated body near the distal end of the elongated body, and the second balloon is disposed about the elongated body proximally to the first balloon, said plurality of infusion lumens includes a first infusion lumen, a second infusion lumen, and a third infusion lumen, and said plurality of infusion ducts includes a first infusion duct disposed near the distal end of the elongated body and in fluid communication with the first infusion lumen, a second infusion duct in fluid communication with the second infusion lumen, and a third infusion duct in fluid communication with the third infusion lumen.

5. The heat exchange catheter of claim 4, wherein the second infusion duct is disposed proximally of the first balloon and distally of the second balloon, and the third infusion duct is disposed proximally of the second balloon.

6. The heat exchange catheter of claim 4, wherein the second infusion duct is disposed in a gap between the first balloon and the second balloon.

7. The catheter of claim 4, wherein the first infusion duct is disposed at a distal tip of the elongated body.

8. The catheter of claim 4, wherein said plurality of infusion lumens further includes a fourth infusion lumen, and said plurality of infusion ducts further includes a fourth infusion duct that is in fluid communication with the fourth infusion lumen.

9. The catheter of claim 8, wherein the first infusion duct is disposed at a distal tip of the elongated body, and the fourth infusion duct is disposed near the distal end of said elongated body between the first balloon and the first infusion duct.

10. The catheter of claim 4, wherein said plurality of inflow ducts further includes a third inflow duct, said plurality of outflow ducts further includes a third outflow duct, and said plurality of heat exchange elements further includes a third balloon disposed proximally of the second balloon and defining with the elongated body a third internal cavity, wherein heat exchange fluid may enter the third internal cavity through the third inflow duct, and wherein the third internal cavity is in fluid communication with the outflow lumen through the third outflow duct.

11. The catheter of claim 10, wherein the first balloon has a diameter of approximately 5 to 9 mm, wherein tie second balloon has a diameter of approximately 5 to 9 mm, and wherein the third balloon has a diameter of approximately 4 to 6 mm.

12. The heat exchange catheter of claim 10, wherein the second infusion duct is disposed proximally of the first balloon and distally of the second balloon, and the third infusion duct is disposed proximally of the second balloon and distally of the third balloon.

13. The heat exchange catheter of claim 10, wherein the second infusion duct is disposed in a gap between the first balloon and the second balloon, and the third infusion duct is disposed in a gap between the second balloon and the third balloon.

14. The catheter of claim 10, wherein the first infusion duct is disposed at a distal tip of the elongated body.

15. The catheter of claim 12, wherein said plurality of infusion lumens further includes a fourth infusion lumen, and said plurality of infusion ducts further includes a fourth infusion duct that is in fluid communication with the fourth infusion lumen.

16. The catheter of claim 15, wherein the fourth infusion duct is disposed proximally of the third balloon.

17. The catheter of claim 15, wherein the first infusion duct is disposed at a distal tip of the elongated body, and the fourth infusion duct is disposed near the distal end of said elongated body between the first balloon and the first infusion duct.

18. The catheter of claim 15, wherein said plurality of infusion lumens further includes a fifth infusion lumen, said plurality of infusion ducts further includes a fifth infusion duct that is in fluid communication with the fifth infusion lumen, the first infusion duct is disposed at a distal tip of the elongated body, and the fifth infusion duct is disposed near the distal end of said elongated body between the first balloon and the first infusion duct.

19. The catheter of claim 10, wherein said plurality of inflow ducts further includes a fourth inflow duct, said plurality of outflow ducts further includes a fourth outflow duct, and said plurality of heat exchange element, further includes a fourth balloon disposed proximally of the third balloon and defining with the elongated body a fourth internal cavity, wherein heat exchange fluid may enter the fourth internal cavity through the fourth inflow duct, and wherein the fourth internal cavity is in fluid communication with the outflow lumen through the fourth outflow duct.

20. The catheter of claim 19, wherein the first balloon has a diameter of approximately 8 to 12 mm, the second balloon has a diameter of approximately 8 to 12 mm, the third balloon has a diameter of approximately 5 to 9 mm, and the fourth balloon has a diameter of approximately 4 to 6 mm.

21. The heat exchange catheter of claim 19, wherein the second infusion duct is disposed proximally of the first balloon and distally of the second balloon, and the third infusion duct is disposed proximally of the second balloon and distally of the third balloon.

22. The heat exchange catheter of claim 19, wherein the second infusion duct is disposed in a gap between the first balloon and the second balloon, and the third infusion duct is disposed in a gap between the second balloon and the third balloon.

23. The catheter of claim 19, wherein the first infusion duct is disposed at a distal tip of the elongated body.

24. The catheter of claim 21, wherein said plurality of infusion lumens further includes a fourth infusion lumen, and said plurality of infusion ducts further includes a fourth infusion duct that is in fluid communication with the fourth infusion lumen.

25. The catheter of claim 24, wherein the fourth infusion duct is disposed proximally of the third balloon and distally of the fourth balloon.

26. The catheter of claim 24, wherein the fourth infusion duct is disposed in a gap between the third balloon and the fourth balloon.

27. The catheter of claim 24, wherein the fourth infusion duct is disposed proximally of the fourth balloon.

28. The catheter of claim 24, wherein the first infusion duct is disposed at a distal tip of the elongated body, and the fourth infusion duct is disposed near the distal end of said elongated body between the first balloon and the first infusion duct.

29. The catheter of claim 25, wherein said plurality of infusion lumens further includes a fifth infusion lumen, and said plurality of infusion ducts further includes a fifth infusion duct that is in fluid communication with the fifth infusion lumen.

30. The catheter of claim 29, wherein the fifth infusion duct is disposed proximally of the fourth balloon.

31. The catheter of claim 29, wherein the first infusion duct is disposed at a distal tip of the elongated body, and the fifth infusion duct is disposed near the distal end of said elongated body between the first balloon and the first infusion duct.

32. The catheter of claim 1, wherein at least one of said plurality of beat exchange elements has a helical configuration that wraps around the elongated body in a series of turns, said configuration having a pitch indicative of a distance between the turns.

33. The catheter of claim 32, wherein the pitch is constant over the length of the at least one heat exchange element, such that the distance between the turns of the at least one heat exchange element remains substantially constant over the length of the at least one heat exchange element.

34. The catheter of claim 32, wherein the pitch varies over the length of the at least one heat exchange element, such that the distance between the turns of the at least one heat exchange element varies over the length of the at least one heat exchange element.

35. The catheter of claim 32, wherein at least one of said plurality of infusion ducts is disposed in a gap between the turns of said at least one heat exchange element.

36. The catheter of claim 1, wherein at least two of said plurality of heat exchange elements have a helical configuration and wrap around the elongated body in a series of turns, each configuration having a pitch indicative of a distance between the turns.

37. The catheter of claim 36, wherein the pitch of one of said at least two heat exchange elements is different than the pitch of at least one other of said at least two heat exchange elements.

38. The catheter of claim 36, wherein the pitch of at least one of said at least two heat exchange elements varies over the length of the at least one heat exchange element.

39. The catheter of claim 2, wherein at least one of said balloons is expandable from a flattened configuration wherein the balloon lies substantially flush with the elongated body to an operational configuration wherein the at least one balloon is inflated by the heat exchange fluid.

40. The catheter of claim 39, wherein an exterior surface of at least one of said balloons is substantially wrinkle-free when the at least one balloon is inflated by the heat exchange fluid.

41. The catheter of claim 2, wherein each of said balloons has a length that maximizes a heat transfer rate without harming the patient.

42. The catheter of claim 41, wherein the length is approximately 58 mm.

43. The catheter of claim 2, wherein at least some of the heat exchange fluid flows in a serial flow path, such that at least some of the heat exchange fluid flows through more than one balloon before returning to the proximal end of the catheter.

44. The catheter of claim 2, wherein at least some of the heat exchange fluid flows in parallel flow paths, such that at least some of the fluid travels through no more than one balloon before returning to the proximal end of the catheter.

45. The catheter of claim 2, wherein the first inflow duct is larger than the second inflow duct.

46. The catheter of claim 1, wherein each of said plurality of heat exchange elements has a cross-sectional size that is no larger than a percentage of a cross-sectional size of the body conduit in which the balloon is positioned.

47. The catheter of claim 46, wherein the percentage is approximately 30% to 75%.

48. The catheter of claim 1, wherein at least one of said plurality of infusion ducts is disposed in a longitudinal side of the elongated body near the distal end of the elongated body.

49. The catheter of claim 1, wherein at least one of said plurality of infusion ducts is disposed at a distal tip of the elongated body.

50. The catheter of claim 1, wherein each of said plurality of heat exchange elements has a flow of the heat exchange fluid, and the flow of the heat exchange fluid in at least one of said plurality of heat exchange elements is balanced relative to the flow in at least one other of said plurality of heat exchange elements.

51. The catheter of claim 1, further comprising a covering disposed over at least a portion of at least one of said plurality of heat exchange elements to facilitate laminar flow around the catheter.

52. The catheter of claim 51, wherein the covering has elastomeric characteristics.

53. The catheter of claim 1, wherein at least one of the plurality of inflow ducts or at least one of the plurality of outflow ducts has the configuration of a longitudinal slot.

54. The catheter of claim 1, wherein one of said plurality of infusion lumens is configured to receive a guidewire, wherein the guidewire is used to stiffen the catheter during insertion of the catheter into the patient, and may be removed after insertion.

55. The catheter of claim 1, wherein at least one of said plurality of infusion ducts is disposed between two of said plurality of heat exchange elements.

56. The catheter of claim 1, wherein at least one of said plurality of heat exchange elements is configured to promote mixing of the heat exchange fluid flowing within the at least one heat exchange element.

57. The catheter of claim 1, wherein the shape of at least one of said plurality of heat exchange elements promotes mixing of the body fluid flowing outside the at least one heat exchange element.

58. The catheter of claim 1, wherein the shape of at least one of said plurality of heat exchange elements promotes residence time of the heat exchange fluid in the at least one heat exchange element.

59. The catheter of claim 1, wherein at least one of said plurality of heat exchange elements has a configuration selected from a group comprising helical, fluted, cylindrical, toroid, and tubular configurations.

60. The catheter of claim 1, wherein at least one of the plurality of heat exchange elements has a configuration that is different than a configuration of at least one other of the plurality of heat exchange elements.

61. The catheter of claim 1, wherein at least one of the plurality of heat exchange elements has a fluted configuration and at least one other of the plurality of heat exchange elements has a helical configuration.

62. The catheter of claim 1, wherein at least one of said plurality of infusion lumens, said outflow lumen, or said inflow lumen has a crescent-shaped or multi-faceted cross-section.

63. The catheter of claim 1, wherein at least one of said plurality of heat exchange elements comprises an array of hollow fibers adapted to transport the heat exchange fluid.

64. The catheter of claim 1, wherein the elongated body further comprises a guidewire lumen extending between the proximal portion and the distal portion of the elongated body.

65. The catheter of claim 1, further comprising an anchor connected with the proximal portion of the elongated body and configured to connect the elongated body with the patient.

66. The catheter of claim 1, wherein said catheter is configured to be incubated into a blood vessel located in the patient's lower central venous system.

67. The catheter of claim 1, wherein said catheter is configured to be inserted into the patient's femoral vein.

68. The catheter of claim 1, wherein the heat exchange fluid is a cooling fluid.

69. The catheter of claim 1, wherein the heat exchange fluid is a heating fluid.

70. The catheter of claim 1, further comprising at least one depth marking disposed on the elongated body that indicates the length of a portion of the catheter that is intubated into the patient.

71. The catheter of claim 70, further comprising a plurality of said depth markings, wherein said markings are spaced along at least the proximal portion of the elongated body, each of said plurality of markings indicating a length of the catheter measured from each marking to the distal end of the catheter.

72. The catheter of claim 70, wherein at least one marking when intubated inside the patient is detectable using X-rays.

73. The catheter of claim 1, further comprising a distal indicator disposed near a distal tip of the catheter, the indicator being detectable using X-rays, such that the position of the distal tip of the catheter relative to a patient's heart, body conduit or other portion of a patient may be determined when the catheter is intubated into the patient.

74. The catheter of claim 1, wherein at least portions of the catheter are provided with properties including thromboresistance.

75. The catheter of claim 74, wherein the thromboresistance property is provided in the form of a coating having thromboresistant characteristics.

76. The catheter of claim 75, wherein the coating includes an anticoagulant.

77. The catheter of claim 75, the coating is adapted to receive an electrical charge providing the thromboresistant properties to the coating.

78. An intra-vascular catheter adapted to exchange heat with a body fluid flowing through a body conduit of a patient, comprising:
- a generally tubular elongated body having a proximal portion with a proximal end and a distal portion with a distal end;
- an inflow lumen extending between the proximal portion and the distal portion of the elongated body;
- an outflow lumen extending between the proximal portion and the distal portion of the elongated body;
- at least one infusion lumen extending between the proximal portion and the distal portion of the elongated body;
- at least one inflow duct in fluid communication with the inflow lumen and disposed on the distal portion of the elongated body;
- at least one outflow duct in fluid communication with the outflow lumen and disposed on the distal portion of the elongated body;
- at least one infusion duct in fluid communication with the infusion lumen and disposed on the distal portion of the elongated body;
- at least one heat exchange element for effecting heat exchange with the body fluid in the body conduit, wherein the at least one heat exchange element extends at least partially along the distal portion of the elongated body, fluidly communicates with the inflow duct through which heat exchange fluid may enter the heat exchange element, and fluidly communicates with the outflow lumen through the outflow duct, such that a heat exchange fluid introduced into the input lumen will enter the at least one heat exchange element through the inflow duct and will exit the at least one heat exchange element through the outflow duct, wherein at least one outflow duct is larger than a corresponding inflow duct.

79. An intra-vascular catheter adapted to exchange heat with a body fluid flowing through a body conduit of a patient, comprising:
- a generally tubular elongated body having a proximal portion and a distal portion with a distal tip;
- an inflow lumen extending between the proximal portion and the distal portion of the elongated body;
- an outflow lumen extending between the proximal portion and the distal portion of the elongated body;
- a first inflow duct, a second inflow duct, and a third inflow duct, each of said first, second and third inflow ducts being disposed on the distal portion of the elongated body;
- a first outflow duct, a second outflow duct, and a third outflow, duct, each of said first, second and third outflow ducts being in fluid communication with the outflow lumen and disposed on the distal portion of the elongated body;
- a first heat exchange element extending at least partially along the distal portion of the elongated body and disposed near the distal tip of the elongated body, the first heat exchange element defining with the elongated body a first internal cavity, wherein the first internal cavity is in fluid communication with the inflow lumen through the first inflow duct, and is in fluid communication with the outflow lumen through the first outflow duct;
- a second heat exchange element extending at least partially along the distal portion of the elongated body and disposed proximally to the first heat exchange element, the second heat exchange element defining with the elongated body a second internal cavity, wherein a heat exchange fluid may enter the second internal cavity through the second inflow duct, and wherein the second internal cavity is in fluid communication with the outflow lumen through the second outflow duct;
- a third heat exchange element extending at least partially along the distal portion of the elongated body and disposed proximally of the second heat exchange element, the third heat exchange element defining with the elongated body a third internal cavity, wherein heat exchange fluid may enter the third internal cavity through the third inflow duct, and wherein the third internal cavity is in fluid communication with the outflow lumen through the third outflow duct;
- a first infusion lumen, a second infusion lumen, and a third infusion lumen, each of said first, second and third infusion lumens extending between the proximal portion and the distal portion of the elongated body;
- a first infusion duct disposed distally of the first heat exchange element and near the distal tip of the elongated body, the first infusion duct being in fluid communication with the first infusion lumen;
- a second infusion duct disposed on the distal portion of the elongated body proximally of the first heat exchange element and distally of tie second heat exchange element, the second infusion duct being in fluid communication with the second infusion lumen; and
- a third infusion duct disposed on the distal portion of the elongated body proximally of the second heat exchange element and distally of the third heat exchange element, the third infusion duct being in fluid communication with the third infusion lumen.

80. The catheter of claim 79, wherein the first infusion duct is disposed at the distal tip of the elongated body.

81. The catheter of claim 79, wherein the first heat exchange element comprises a first balloon having a diameter of approximately 5 to 9 mm, wherein the second heat exchange element comprises a second balloon having a diameter of approximately 5 to 9 mm, and wherein the third heat exchange element comprises a third balloon having a diameter of approximately 4 to 6 mm.

82. The catheter of claim 79, wherein at least one of said first, second and third heat exchange elements has a helical configuration that wraps around the distal portion of the elongated body in a series of turns.

83. The catheter of claim 79, wherein at least one of said first, second and third heat exchange elements has a substantially straight configuration.

84. A method for controlling a temperature of a patient and accessing a body fluid flowing through a body conduit of the patient, comprising the acts of:
- using an intravascular catheter to access the body fluid, the intravascular catheter comprising:
  - an elongated body;
  - at least one heat exchange element disposed about the elongated body, each heat exchange element having an exterior surface and being in a heat exchange relationship with the body fluid; and a plurality of infusion lumens for accessing the body fluid; and circulating a heat exchange fluid through at least one heat exchange element to effect heat transfer across the exterior surface with the body fluid flowing through the body conduit, wherein said at least one heat exchange element includes two to four expandable balloons, the balloons being spaced along at least a distal portion of the elongated body such that at least two of said balloons define a gap, said plurality of infusion lumens includes three to five infusion lumens, and said catheter further comprises a plurality of infusion ducts, wherein each infusion lumen communicates with the body fluid through one of said plurality of infusion ducts, wherein at least one of said plurality of infusion ducts is disposed in said gap, and/wherein at least one of said plurality of infusion ducts is disposed near a distal end of the catheter.

85. The method of claim 84, wherein the step of using an intravascular catheter to access the body fluid comprises the step of intubating the catheter into the patient's venous system.

86. The method of claim 85, wherein the step of intubating the catheter into the patient's venous system comprises the step of inserting the catheter into the patient's femoral vein.

87. The method of claim 84, wherein the step of using an intravascular catheter to access the body fluid comprises the steps of selecting the body conduit, measuring a cross-sectional dimension of the body conduit, and selecting the catheter having a size such that no more than approximately a percentage of the body conduit's cross-section is blocked when the catheter is inserted into the body conduit.

88. The method of claim 84, wherein the step of using an intravascular catheter to access the body fluid comprises the steps of selecting the body conduit, measuring a length of the body conduit, and selecting the catheter having a length such that the heat exchange elements are disposed along approximately a percentage of the length of the body conduit.

89. The method of claim 84, wherein each heat exchange element is sized such that when the catheter is inserted into the body conduit of the patient, no more than approximately 30% to 75% of the body conduit is blocked at each respective heat exchange element location.

90. The method of claim 84, further comprising the step of infusing a fluid into the body conduit via at least one of the plurality of infusion lumens.

91. The method of claim 84, further comprising the step of expanding at least one heat exchange element with the heat exchange fluid after the catheter is intubated into the patient.

92. The method of claim 84, wherein the heat exchange relationship of the heat exchange element with the central venous system is maintained for a duration of about one hour to about twenty-nine days.

93. The method of claim 84, further comprising the step of suturing or otherwise affixing the catheter to the patient.

* * * * *